United States Patent [19]

Kelman

[11] Patent Number: 4,508,216

[45] Date of Patent: Apr. 2, 1985

[54] HOUSING FOR AN INTRAOCULAR LENS AND METHOD OF USING THE SAME

[76] Inventor: Charles D. Kelman, The Empire State Bldg., 350 Fifth Ave., New York, N.Y. 10118

[21] Appl. No.: 513,682

[22] Filed: Jul. 14, 1983

[51] Int. Cl.³ .......................... A61F 1/16; A61F 1/18; B65D 25/54; G01F 23/00; G02B 27/00

[52] U.S. Cl. .................................. 206/5.1; 206/45.34; 220/82 A; 350/242

[58] Field of Search .............................. 206/5.1, 45.34; 220/82 A; 350/232, 115, 243; 73/312

[56] References Cited

U.S. PATENT DOCUMENTS

| | | | |
|---|---|---|---|
| 3,052,158 | 9/1962 | Sonni | 220/82 A |
| 3,080,964 | 3/1963 | Robinson et al. | 220/82 A |
| 3,397,935 | 8/1968 | Natsume | 220/82 A |
| 4,173,281 | 11/1979 | Trought | 206/45.34 |
| 4,269,307 | 5/1981 | LaHaye | 206/45.34 |
| 4,415,076 | 11/1983 | Campbell | 220/82 A |
| 4,423,809 | 1/1984 | Mazzocco | 206/45.34 |

Primary Examiner—William T. Dixson, Jr.
Attorney, Agent, or Firm—Henry Sternberg

[57] ABSTRACT

A housing for an intraocular lens having opposed walls and having a lens in at least one of these walls which is the same in magnitude and opposite in sign to the optical power of the lens intended to be housed therein. The housing bears indicia of the optical magnitude and sign of the lens intended to be housed therein. A surgeon can ascertain whether the intended lens is in the housing by viewing an object through the housing walls and through the lens housed therein. There will be substantially no optical distortion if the intended lens is in the housing.

14 Claims, 4 Drawing Figures

HOUSING FOR AN INTRAOCULAR LENS AND METHOD OF USING THE SAME

This invention relates to a housing for an intraocular lens and to a method of ascertaining whether an intraocular lens has a desired optical power.

It is important for a surgeon to be able to determine whether the intraocular lens which he is about to implant into a patient's eye has the correct optical power. The surgeon is always concerned that the lens manufacturer may have mistakenly placed the wrong lens into a lens container or housing marked with a given optical power. Once the lens has been implanted in the eye there is no known method for accurately determining the optical power of the lens. Of course, if a lens with the wrong power were implanted, it would cause serious hardship for both the surgeon and the patient.

It is an object of the present invention, therefore, to provide a new and improved housing for an intraocular lens which avoids one or more of the limitations and disadvantages of prior such housings.

It is another object of the invention to provide a new and improved housing for an intraocular lens of simple construction for accurately indicating the correctness of the optical power of the lens therein while it is still in its sterilized container or housing and just prior to removing it from the housing for implantation in the eye.

It is another object of the invention to provide a new and improved method of ascertaining whether an intraocular lens has a desired optical power which avoids one or more of the disadvantages and limitations of prior methods.

It is another object of the invention to provide a new and improved method of ascertaining whether an intraocular lens has a desired optical power which can be performed in a simple manner.

In accordance with the invention, a housing for an intraocular lens having an optic comprises at least a pair of opposed walls enclosing the lens within the housing. The walls comprise lens means having an optical power which is substantially of the same magnitude as but opposite in sign to the optical power of the lens intended to be housed. The lens means is positioned substantially to coincide with the optic of the housed lens when viewed along the optical axis thereof so that a viewer can see through the housing without substantial distortion if the intended lens is in the housing.

Also in accordance with the invention, a method of ascertaining whether an intraocular lens having an optic has a desired optical power comprises housing an intraocular lens intended to have a desired optical power in a housing having at least a pair of opposed walls enclosing the lens within the housing. The walls comprise lens means having an optical power which is opposite to the optical power of the lens intended to be housed. The lens means is positioned substantially to coincide with the optic of the housed lens when viewed along the optical axis thereof. The method also comprises viewing an object through the lens means of the walls and through the optic of the lens housed in the housing so that a viewer can see through the housing without substantial distortion if the intended lens is in the housing.

For a better understanding of the present invention, together with other and further objects thereof, reference is made to the following description taken in connection with the accompanying drawings, and its scope will be pointed out in the appended claims.

Figure 1:
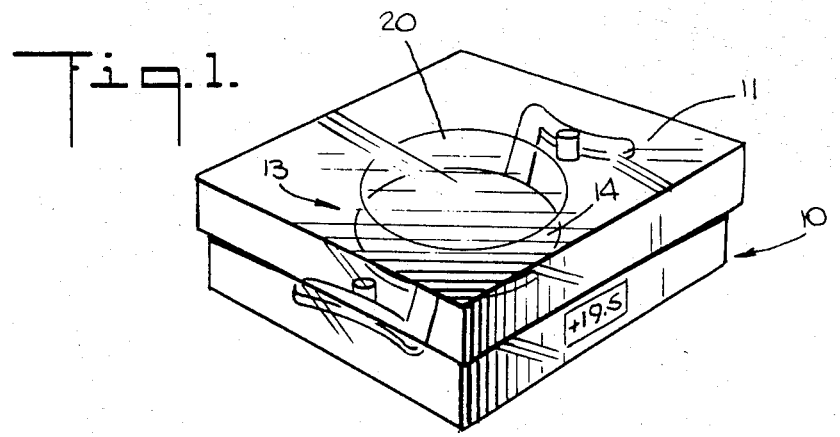
FIG. 1 is a perspective view of a housing constructed in accordance with the invention housing a lens therein.
Figure 2:
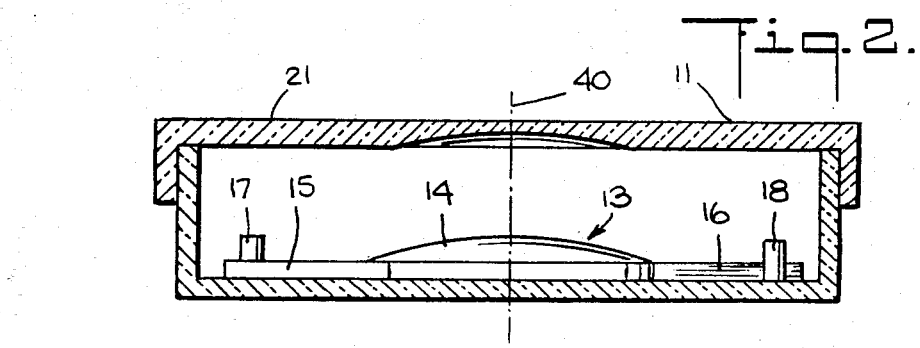
FIG. 2 is a sectional view of the FIG. 1 housing with a lens therein, shown in side elevational view.

Referring now more particularly to FIGS. 1 and 2 of the drawings, there is represented a housing for an intraocular lens comprising at least a pair of walls 11, 12, that is, the top and bottom walls, enclosing a lens 13 within the housing 10. The lens 13 may be of any suitable intraocular type having, for example, a lens body 14 and a pair of position-fixation legs 15, 16 which are positioned around projections 17, 18 extending upwardly, for example, from the bottom wall 12 of the housing to maintain the lens 13 in position in the housing. The top and bottom walls 11, 12 of the housing preferably are of transparent plastic material.

The walls 11, 12 jointly comprise light-transmissive lens means having an optical power which is opposite to the optical power of the lens intended to be housed and may jointly comprise portions having zero optical power. The top wall 11 and the bottom wall 12 are represented in fragmentary sectional view, to an enlarged scale, in FIG. 2, and the lens means comprises an inexpensive lens 20 having an optical power which is substantially the same in magnitude and opposite in sign to the optical power of the lens intended to be housed. Due to this reversal of optical properties, the optical properties of the lens means and of the housed lens cancel each other out, if the intended lens is in the housing. According to the preferred embodiment represented in FIG. 2, a portion of the wall 11, for example, portion 21, has zero optical power, and the wall 12 has zero optical power. The lens means 20 preferably is molded integrally with the wall 11 and may be in the form of an arcuate indentation in the surface of the wall 11. Alternatively, the lens means 20 may, for example, be a separate lens member attached to one of the surfaces of wall 11 or fitted into an opening in wall 11 (not shown).

The lens means 20 preferably is of substantially the same size as the lens 13 in the plane of the lens normal to the optical axis thereof represented in FIG. 1 by broken line 40, and the lens means 20 is positioned in the wall 12 substantially to coincide with the housed lens 13 when viewed along the optical axis thereof so that a viewer can see through the housing without substantial distortion if the intended lens is in the housing.

As indicated in FIG. 1 the housing bears indicia, for example, plus (+) 19.5 representing the optical power of the lens 13 intended to be housed therein which may, for example, be a converging lens. The lens means 20 may, for example, be a diverging lens having an optical power of minus (−) 19.5 diopters.

Figure 3:
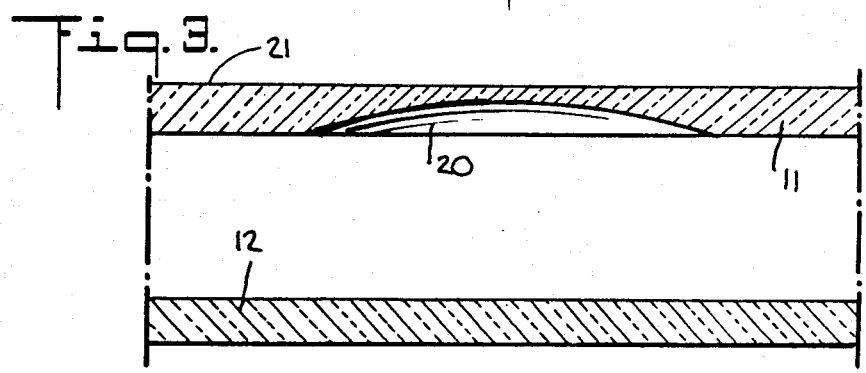
FIG. 3 is a fragmentary sectional view, to an enlarged scale, of two opposed walls of the FIG. 1 housing.
Figure 4:
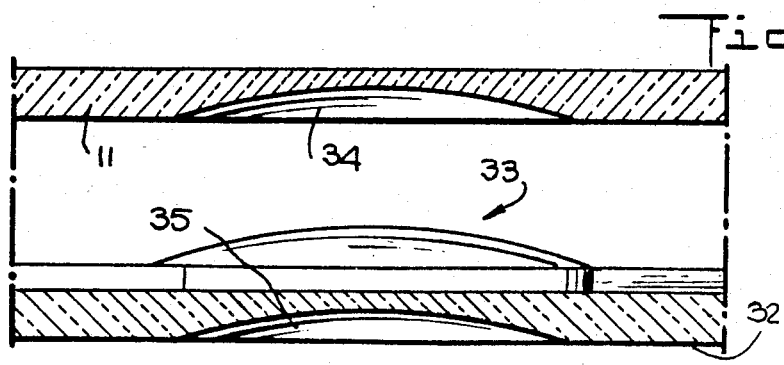
FIG. 4 is a fragmentary sectional view, to an enlarged scale, of another housing constructed in accordance with the invention housing a lens therein shown in side elevational view.

Referring now more particularly to FIG. 3 of the drawings, top and bottom walls 31, 32 of a housing similar to the FIG. 1 housing 10 are represented in fragmentary sectional view. A lens 33 similar to the lens 13 is also represented in FIG. 3. A portion 34 of the lens means of the housing is disposed in the top wall 31 and a portion 35 of the lens means of the housing is disposed in the bottom wall 32. The lens portions 34, 35 jointly comprise lens means having an optical power of substantially the same magnitude but opposite in sign to the lens 33 intended to be housed in the housing.

A method of ascertaining whether the intraocular lens 13 has a desired optical power comprises housing the intraocular lens 13 intended to have a desired optical power, for example, plus (+) 19.5 diopters, in the housing 10 having at least the pair of opposed walls 11, 12 enclosing the lens within the housing. The method also includes the step of viewing an object or objects through the lens means of the walls and through the optic of the lens housed in the housing so that a viewer can see through the housing, i.e. along the optical axis 40, without substantial distortion, if the intended lens is in the housing. The method also includes the step of reading the indicia on the container.

If just prior to removal of the lens 13 from the housing for insertion into a patient's eye, the surgeon views an object through the lens means 20 and through the optic of lens 13 while the lens 13 is positioned in the housing (bearing the indicia "+19.5"), the surgeon can be assured by the fact that there is substantially no distortion that a lens having an optical power of plus (+) 19.5 diopters is enclosed in the housing.

The lens housing is such that the intraocular lens housed therein has its optic positioned coaxially with the portion of the housing wall which resembles an optic so that the surgeon by merely looking through the transparent top and bottom walls 11, 12 will be looking through both the optic of the intraocular lens and the optic in the housing wall which overlies it. If the lens in the housing is the correct lens then the surgeon's view will be undistorted since the top optics will nullify each other, one being positive and one being negative by the same amount. If, on the other hand, an improper lens is in the housing, then the surgeon will have his view substantially distorted and this will be the case even if there is only a slight difference between the lens which is in the housing and the one which should be in the housing. For example, a difference of one-half diopter is sufficient for the surgeon immediately to ascertain that the improper lens is in the housing.

When the housing walls 11, 12 are transparent and have zero optical power in portions other than the lens means 20, the surgeon may view an object partially through the lens means 20 and the optic of lens 13 and partially through the transparent portions of the walls 11, 12 having zero optical power for comparison of the view through the lens means 20 and the optic of lens 13 with the adjacent view through the portions of walls 11, 12 having zero optical power to facilitate his determination of whether there is any distortion of the view through the lens means 20 and the optic of lens 13.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A housing for an intraocular lens having an optic comprising:
   at least a pair of opposed walls adapted to enclose the lens within the housing, said walls comprising lens means having an optical power which is substantially of the same magnitude as but opposite in sign to the optical power of the lens intended to be housed and said lens means being positioned substantially to coincide with the optic of the housed lens when viewed along the optical axis thereof so that a viewer can see through said lens means of the housing and through the lens housed therein without substantial distortion if the intended lens is in the housing.

2. A housing in accordance with claim 1 in which said lens means comprises a lens in one of said walls.

3. A housing in accordance with claim 2 in which said lens means comprises a light-transmissive portion in the other of said pair of walls.

4. A housing in accordance with claim 3 in which said light-transmissive portion is a transparent portion of said other wall having zero optical power.

5. A housing in accordance with claim 1 wherein said lens means exhibits the optical characteristics of a diverging lens, said lens which is intended to be housed being a converging lens.

6. A housing in accordance with claim 1 wherein said walls are substantially parallel and a portion of said lens means is located in each of said pair of opposed parallel walls.

7. A housing in accordance with claim 1 in which said walls are transparent.

8. A housing in accordance with claim 7 wherein said lens means is molded integrally with one of said walls.

9. A housing in accordance with claim 1 which bears indicia representing the optical power of the lens intended to be housed therein.

10. A housing in accordance with claim 1 in which the optic of the housed lens has a circular periphery and in which said lens means has substantially the same diameter as the optic of the housed lens.

11. A housing in accordance with claim 10 in which said opposed walls of said housing have opposed transparent portions having zero optical power through which a viewer can see.

12. A method of ascertaining whether an intraocular lens having an optic has a desired optical power comprising:
   housing an intraocular lens intended to have a desired optical power in a housing having at least a pair of opposed walls enclosing the lens within the housing, the walls comprising lens means having an optical power which is of substantially the same magnitude as but opposite in sign to the optical power of the lens intended to be housed and the lens means being positioned in the walls substantially to coincide with the optic of the housed lens when viewed along the optical axis thereof; and
   viewing an object through the lens means of the walls and through the optic of the lens housed in said housing so that a viewer can see through the housing without substantial distortion if the intended lens is in the housing.

13. A method in accordance with claim 12 in which said housing bears indicia representing the optical power of the lens intended to be housed therein and which includes the step of reading the indicia.

14. A method in accordance with claim 12 in which the opposed walls of the housing have opposed transparent portions having zero optical power and which includes the step of viewing the object partially through the portions of the opposed walls having zero optical power.

* * * * *